(12) United States Patent
Rose et al.

(10) Patent No.: US 7,423,170 B2
(45) Date of Patent: Sep. 9, 2008

(54) ANTICANCER AGENTS BASED ON REGULATION OF PROTEIN PRENYLATION

(75) Inventors: Seth D. Rose, Tempe, AZ (US); Scott R. Lefler, Tempe, AZ (US); Steven R. Ottersberg, Tempe, AZ (US); Ann Y. Kim, Glendale, AZ (US); Karl J. Okolotowicz, Tempe, AZ (US); Rosemarie F. Hartman, Tempe, AZ (US)

(73) Assignee: Arizona Biomedical Research Commission, Phoenix, AZ (US)

( * ) Notice: Subject to any disclaimer, the term of this patent is extended or adjusted under 35 U.S.C. 154(b) by 124 days.

(21) Appl. No.: 11/275,662

(22) Filed: Jan. 23, 2006

(65) Prior Publication Data

US 2006/0111329 A1  May 25, 2006

Related U.S. Application Data

(62) Division of application No. 09/983,232, filed on Oct. 23, 2001, now Pat. No. 7,019,031.

(60) Provisional application No. 60/241,955, filed on Oct. 23, 2000.

(51) Int. Cl.
| C07C 69/007 | (2006.01) |
| C07C 69/017 | (2006.01) |
| A01N 57/14  | (2006.01) |
| A01N 41/04  | (2006.01) |
| A01N 41/10  | (2006.01) |

(52) U.S. Cl. .................. 560/150; 560/156; 560/183; 560/219; 560/225; 560/226; 514/533; 514/423; 514/408; 514/315; 514/357; 514/438; 514/471; 514/534; 549/61; 549/62; 549/68; 549/190

(58) Field of Classification Search ............ 514/533, 514/423, 408, 315, 357, 438, 471, 534; 549/61, 549/62, 68, 190; 560/150, 156, 183, 219, 560/225, 226
See application file for complete search history.

(56) References Cited

U.S. PATENT DOCUMENTS

| 4,235,923 A | 11/1980 | Durham |
| 4,900,749 A | 2/1990 | Matsumoto et al. |
| 5,733,911 A | 3/1998 | Eilon et al. |
| 6,166,074 A | 12/2000 | Pettersen et al. |

FOREIGN PATENT DOCUMENTS

| EP | 0147217 | 7/1985 |
| EP | 0170048 A2 | 2/1986 |
| EP | 0248597 | 12/1987 |
| EP | 0355315 | 10/1989 |
| EP | 0410244 A1 | 1/1991 |
| EP | 0534546 A1 | 3/1993 |
| EP | 0752465 A1 | 1/1997 |
| GB | 1599532 | 10/1981 |
| JP | 07002821 | 1/1995 |
| WO | 9115473 | 10/1991 |
| WO | 9322304 | 11/1993 |
| WO | 0004032 | 1/2000 |
| WO | 0033826 | 6/2000 |

OTHER PUBLICATIONS

Nishizawa et al., Tetrahedron Letters, 1983, 24(25), pp. 2581-2584; Abstract only.*
Jagodzinski et al., Khimiya Ceterotsiklicheskikh Soedinenii, 1988, 3, pp. 410-417: Abstract only.*
Hara, M. et al., Identification of Ras Farnesylation Inhibitors by Microbial Screening, Proc. Natl. Acad. Sci, USA, vol. 90: 2281-2285 (1993).
Karl J. Okolotowicz, Wei-Jen Lee, Rosemarie F. Hartman, Scott R. Lefler, and Seth D. Rose, Inactivation of Protein Farnesyltransferase by Active-Site-Targeted Dicarbonyl Compounds, Arch. Pharm. Pharm. Med. Chem. 334, 194-202, 9 pages, 2001.
Journal of the Chemical Society, The Oxidation of -Unsaturated Ketones with Alkaline Hydrogen Peroxide, pp. 665-670. 1949.
Journal of the American Chemical Society, Epoxidation of Alkenes with Bicarbonate-Activated Hydrogen Peroxide, vol. 122, pp. 3220-3221, 2000.

(Continued)

*Primary Examiner*—Elvis O Price
(74) *Attorney, Agent, or Firm*—Banner & Witcoff, Ltd.

(57) ABSTRACT

Oncoproteins such as Ras and RhoB are known to induce cell division in an unrestrained manner when such proteins are localized at the inner surface of a cancer cell membrane. The localization is effected by the prenylation reaction, whereby a hydrophobic group (e.g. a farnesyl group) is attached to the protein in the presence of an enzyme (e.g. farnesyl protein transferase). Deactivation of the prenylation enzyme through covalent modification can therefore ultimately result in the mitigation and/or cessation of cancer cell growth. Various prenylation inhibitors having the necessary structural groups to bond covalently, or essentially irreversibly, to the prenylation enzyme include carbonyl or thiocarbonyl compounds (or masked versions of these compounds) and alpha oxo-epoxides bonded to a hydrophobic, substrate-mimicking group. The carbonyl or thiocarbonyl compounds also contain a nucleofugal atom or group to enhance the tendency to form covalent bonds.

4 Claims, No Drawings

OTHER PUBLICATIONS

Tetrahedron, Enhanced disatereoselectivity in the addition of ester enolate to optically active ,-epoxyaldehydes obtained from nerol and geraniol, vol. 52, No. 27, pp. 9047-9056, 1996.

Journal of the American Chemical Society, Catalytic Asymmetric Epoxidation and Kinetic Resolution: Modified Procedures Including in Situ Derivatization, vol. 109, pp. 5765-5780, 1987.

* cited by examiner

ANTICANCER AGENTS BASED ON REGULATION OF PROTEIN PRENYLATION

CROSS-REFERENCE TO RELATED APPLICATIONS

This application is a division of application Ser. No. 09/983,232, now U.S. Pat. No. 7,019.031, filed Oct. 23, 2001, which claims priority to Provisional Application Ser. No. 60/241,955, filed Oct. 23, 2000.

FIELD OF THE INVENTION

The present invention relates to the prevention and/or treatment of cancer by inhibiting enzyme-catalyzed prenylation reactions that allow localization of Ras, RhoB, and other proteins at the inner surfaces of cancer cell membranes and other intracellular locations, thereby causing unrestrained cell division.

BACKGROUND OF THE INVENTION

Approximately 25% of all human cancers result from a mutant gene that encodes a mutant form of the protein known as Ras. In cancer cells, Ras activates the cells to divide in an unrestrained manner. To induce cell division, Ras must be localized at the inner surface of the cancer cell membrane. This membrane localization of Ras is effected by attachment of a hydrophobic group, typically the farnesyl group, but possibly the related geranylgeranyl group. In either case, the group becomes attached to Ras enzymatically in a process known as prenylation. Thus, interference with prenylation of Ras has the potential to prevent Ras localization at the inner surface of the cancer cell membrane, resulting in the cessation of unrestrained cell division and/or reversion of the cancer cell to a normal phenotype.

The enzyme that attaches the farnesyl group to Ras, RhoB, and other proteins to facilitate the proper localization of these proteins in the cell is farnesyl protein transferase, also known as protein farnesyl transferase (referred to here as FTase). The farnesyl group becomes attached to Ras, RhoB, and other proteins by reaction with farnesyl diphosphate, also known as farnesyl pyrophosphate (referred to here as FPP). In other words, FTase catalyzes the reaction illustrated below for the Ras protein, in which the protein becomes attached to the farnesyl group by displacement of pyrophosphate ($P_2O_7^{4-}$, referred to here as $PP_i$):

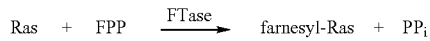

Thus, a key target in a strategy to retard cancer cell proliferation is the enzyme FTase. By regulating FTase activity, Ras farnesylation, RhoB farnesylation and geranylgeranylation, and the prenylation of other proteins can be controlled. This can alter the intracellular distribution of these proteins and in turn prevent cancer cells from proliferating. Because normal cells also require FTase activity, the optimal regulation of prenyltransferase activity must be determined empirically.

Many substances are known to block FTase activity and prevent farnesylation of cellular proteins. These include inhibitors of the enzyme FTase, which generally operate by blocking the binding of proteins to be prenylated, FPP, or both, to the FTase active site. Without the ability of the normal substrates (e.g. Ras and FPP) to bind to FTase, this enzyme can no longer transfer the farnesyl group from FPP to Ras. In general, inhibitors structurally mimic one or both of the natural substrates of the enzyme, in this case Ras and/or FPP. For conventional inhibitors, their binding to FTase is reversible and noncovalent (i.e. the binding of the inhibitor to FTase does not involve the formation of covalent bonds). Instead, hydrophobic forces, hydrogen bonding, electrostatic attraction, etc. are principally responsible for binding of the inhibitor to the enzyme FTase. These binding forces allow the inhibitor to block the site on FTase where the normal substrates need to bind for farnesylation of Ras to occur.

It would therefore be desirable to develop a method of preventing, substantially irreversibly, FTase from farnesylating Ras and, more generally, preventing other prenylation enzymes from promoting the inner cell membrane localization of oncoproteins. Interaction of FTase, for example, with substances that covalently modify the active site of FTase should result in an enzyme with an essentially permanent reduction in catalytic ability. In principle, and in contrast to conventional enzyme deactivation, the covalent attachment can be irreversible or nearly irreversible. The desirable characteristics of a prenylation enzyme inhibitor may include both a substrate-mimicking group as well as a group having the ability to bond covalently to the enzyme at or near its active site.

SUMMARY OF THE INVENTION

The present invention is directed to methods for inhibiting a prenylation enzyme In one embodiment, the method comprises contacting a prenylation enzyme with a prenylation enzyme inhibitor of the following structural Formula I:

(Formula I)

or a pharmaceutically acceptable salt, prodrug, or ester thereof, where $A_1$, $A_2$, and $A_3$ are independently selected from the group consisting of hydrogen, alkyl, alkoxy, alkoxyalkyl, aryloxy, cycloalkoxy, alkylthio, alkenyl, alkynyl, cycloalkyl, haloalkyl, alkanoyl, aroyl, aminocarbonyl, aminoalkanoyl or optionally substituted aminoalkanoyl, carbocycloalkyl or optionally substituted carbocycloalkyl, heterocyclo or optionally substituted heterocyclo, heteroaryl or optionally substituted heteroaryl, aryl, aralkyl, (heterocyclo)alkyl, (heteroaryl)alkyl, alkoxycarbonyl, alkylcarbonyloxy, alkoxyalkanoyl, and carboxyalkyl, and $A_4$ is selected from the group consisting of hydrogen, alkyl, alkoxy, alkoxyalkyl, aryloxy, cycloalkoxy, alkylthio, alkenyl, alkynyl, cycloalkyl, haloalkyl, alkanoyl, aroyl, aminocarbonyl, aminoalkanoyl or optionally substituted aminoalkanoyl, carbocycloalkyl or optionally substituted carbocycloalkyl, heterocyclo or optionally substituted heterocyclo, heteroaryl or optionally substituted heteroaryl, aryl, aralkyl, (heterocyclo)alkyl, (heteroaryl)alkyl, alkoxycarbonyl, alkoxyalkanoyl, carboxyalkyl, amino or substituted amino, amido or substituted amido, and alkanoylamido, with the proviso that $A_1$, $A_2$, $A_3$, and $A_4$ are not all hydrogen. In a preferred embodiment, $A_1$, $A_2$, $A_3$, and $A_4$ are independently selected from the group consisting of hydrogen, alkyl, alkenyl, alkynyl, aryl, aralkyl. In another preferred embodiment, at least one of $A_1$, $A_2$, $A_3$, and $A_4$ is a branched alkenyl, which may be specifically a farnesyl or geranylgeranyl group. In another preferred embodiment, the group $A_4$ is selected from the group consisting of hydrogen, alkyl (e.g. methyl), haloalkyl (e.g. trichloromethyl, trifluoromethyl, perfluoroethyl), aryl (e.g. phenyl), and heteroaryl (e.g. 4-pyridyl).

In another preferred embodiment, the prenylation enzyme inhibitor according to the method has the following structural Formula II:

$$A\text{-}Y\text{—}(C\text{=}Z)\text{—}CX_1X_2X_3 \qquad \text{(Formula II)}$$

or a pharmaceutically acceptable salt, prodrug, or ester thereof, where Y is a heteroatom or heteroatomic group selected from the group consisting of O, NH, NA', and S; where, when Y is O, A and A' are independently selected from the group consisting of hydrogen, alkyl, alkoxyalkyl, alkylthio, alkenyl, alkynyl, cycloalkyl, haloalkyl, carbocycloalkyl or optionally substituted carbocycloalkyl, heterocyclo or optionally substituted heterocyclo, heteroaryl or optionally substituted heteroaryl, aryl, aralkyl, (heterocyclo)alkyl, (heteroaryl)alkyl, carboxyalkyl, amino or substituted amino, amido or substituted amido, and alkanoylamido;

when Y is S, A and A' are independently selected from the group consisting of hydrogen, alkyl, alkoxy, alkoxyalkyl, aryloxy, cycloalkoxy, alkylthio, alkenyl, alkynyl, cycloalkyl, haloalkyl, carbocycloalkyl or optionally substituted carbocycloalkyl, heterocyclo or optionally substituted heterocyclo, heteroaryl or optionally substituted heteroaryl, aryl, aralkyl, (heterocyclo)alkyl, (heteroaryl)alkyl, carboxyalkyl, amino or substituted amino, amido or substituted amido, and alkanoylamido; and, when Y is NH or NA', A and A' are independently selected from the group consisting of hydrogen, alkyl, alkoxy, alkoxyalkyl, aryloxy, cycloalkoxy, alkylthio, alkenyl, alkynyl, cycloalkyl, haloalkyl, alkanoyl, aroyl, aminocarbonyl, aminoalkanoyl or optionally substituted aminoalkanoyl, carbocycloalkyl or optionally substituted carbocycloalkyl, heterocyclo or optionally substituted heterocyclo, heteroaryl or optionally substituted heteroaryl, halo, aryl, aralkyl, (heterocyclo)alkyl, (heteroaryl)alkyl, alkoxycarbonyl, alkylcarbonyloxy, alkoxyalkanoyl, carboxyalkyl, amino or substituted amino, amido or substituted amido, and alkanoylamido;

Z is oxygen or sulfur; and, $X_1$, $X_2$, and $X_3$ are independently selected from the group consisting of hydrogen, oxygen, halogen, organosulfonyloxy, bromobenzenesulfonyloxy, methanesulfonyloxy, trifluoromethanesulfonyloxy, acyloxy, aryloxy, imidazolyl, —O—N=O, —$NO_2$, —$OSO_3^-$, and —$OPO_2(OH)^-$, with the proviso that $X_1$, $X_2$, and $X_3$ are not all hydrogen. In a preferred embodiment, A, and optionally A', are independently selected from the group consisting of hydrogen, alkyl, alkenyl, alkynyl, aryl, aralkyl. In another preferred embodiment, at least one of A, and optionally A', is a branched alkenyl, which may be specifically a farnesyl or geranylgeranyl group. Preferably, at least one of $X_1$, $X_2$, and $X_3$ is a nucleofugal group capable of bonding with the active site of a prenylation enzyme.

According to the possibilities for Formula II, there exists a carbonyl variation, where Z is oxygen, and also a thiocarbonyl variation, where Z is sulfur. In the case of the carbonyl variation, a preferred class of prenylation inhibitors is obtained when $X_1$ is oxygen, such that the inhibitor will now have two carbonyl functions, and $X_2$ is methyl. These preferred compounds may also be categorized as pyruvic acid derivatives.

In another embodiment, a method of screening compounds as potential anti-tumor agents comprises contacting a prenylation enzyme with a test compound according to Formula I or Formula II. The method further comprises measuring prenylation activity of the enzyme to identify candidate anti-tumor agents. In a more specific embodiment, prior to the contacting step, a natural substrate of the prenylation enzyme (e.g. farnesyl pyrophosphate and/or geranylgeranyl pyrophosphate) is added to the test compound to compete therewith and indicate the specificity of the test compound for the prenylation enzyme.

In another embodiment, a method of inhibiting the growth of a cancer cell comprises contacting the cancer cell with a prenylation enzyme inhibitor according to Formula I or Formula II, where the growth of the cancer cell is inhibited.

In another embodiment, a pharmaceutically acceptable formulation comprises a compound according to Formula I or Formula II, and a pharmaceutically acceptable carrier.

These and other embodiments are described below in the detailed description of the invention.

DETAILED DESCRIPTION OF THE INVENTION

The present invention may hamper or prevent the proliferation of cancer cells, possibly resulting in a decrease in tumor size and/or disappearance of the cancer, to the benefit of cancer patients. It may act by interference with cancer cell biochemistry, in which the enzyme farnesyl protein transferase, geranylgeranyl protein transferase, and/or some other prenylation enzyme acts on the oncogenic Ras protein, RhoB protein, or some other growth-related cellular protein. Alteration of the ratio of farnesylated RhoB to geranylgeranylated RhoB, for instance, through the action of farnesyl protein transferase inhibitors, is thought to have a profound effect on cancer cell proliferation. The present invention may alter the farnesylation:geranylgeranylation ratio through the selective regulation of prenylation enzyme activity by covalent modification of the active site of prenylation enzymes rather than reversible inhibition of these enzymes, as is the current practice with farnesyl protein transferase reversible inhibitors.

The present invention is based on the effectiveness of prenylation enzyme inhibitors for ultimately reducing and/or terminating cancer cell proliferation through covalent or essentially irreversible modification of the enzyme. The potential advantages of the present invention over reversible inhibitors of prenyltransferase are: (1) buildup of unused substrate (e.g. FPP, Ras and RhoB proteins) cannot reverse the covalent bonding of this invention in the way reversible inhibitors can be displaced by unused substrates, making the present invention more effective; and (2) the effectiveness of periodic dosing with compounds of the present invention, in contrast to the need for the constant presence of reversible inhibitors, may (i) adjust the activity level of the enzyme, decreasing toxic side effects in the patient; and (ii) minimize the ability of the cancer cell to become resistant to the therapy.

The present invention can reduce or eliminate the unrestrained proliferation of cancer cells through the inhibition of enzymes affecting biochemical reactions in these cells. The specificity of the inhibitor for the target prenylation enzyme can be optimized through two parameters: (1) structural features, including structural similarity to the normal substrates (e.g. FPP and/or Ras), that direct or otherwise favor the binding of the inhibitor to the active site of enzyme, and (2) a reactivity that is appropriate for the chemical groups of the prenylation enzyme, particularly those that participate in the actual process catalyzed by the prenylation enzyme (e.g. those chemical groups that directly participate in the transfer of the farnesyl group of FPP to Ras). The structurally similar feature can be a hydrophobic component having a high affinity for the active site of the enzyme. For example, the active site of FTase is hydrophobic, which favors binding to its natural substrate FPP, also containing a hydrophobic region (i.e. the farnesyl group). Therefore, hydrophobic inhibitors that also contain an alpha-oxo epoxide or a carbon atom bearing at least one nucleofugal atom, where the carbon atom is bonded to a carbonyl (C=O) group or thiocarbonyl (C=S) group, or masked form of an alpha-oxo epoxide, carbonyl, or thiocarbonyl group, such as a group that will convert to a carbonyl or thiocarbonyl group at physiological conditions, are in many cases sufficiently reactive with the prenylation enzyme to inhibit its activity.

The term "alkyl," as used alone or in combination herein, refers to an unsubstituted or optionally substituted, straight, or branched chain saturated hydrocarbon group containing from one to twenty-five carbon atoms, preferably from one to fifteen carbons, such as methyl, ethyl, n-propyl, n-butyl, pentyl, hexyl, heptyl, octyl, the various branch chain isomers thereof, such as isopropyl, isobutyl, sec-butyl, tert-butyl, isohexyl and the like. The alkyl group may be optionally substituted by one or more substituents, and generally no more than three, and most often just one substituent. Preferred optional substituents include halo, alkoxy, amino, mono- and di-substituted amino, aryl, carboxylic acid, heterocyclo, heteroaryl, cycloalkyl, hydroxy, trifluoromethoxy and the like.

The term "lower alkyl," as used alone or in combination herein, refers to such alkyl groups containing from one to five carbon atoms.

The term "alkoxy," as used alone or in combination herein, refers to an alkyl group, as defined above, covalently bonded to the parent molecule through an —O— linkage, such as methoxy, ethoxy, propoxy, isopropoxy, butoxy, t-butoxy and the like.

The term "alkoxyalkyl," as used alone or in combination herein, refers specifically to an alkyl group substituted with an alkoxy group.

The term "aryloxy," as used alone or in combination herein, refers to an aryl group, as defined below, covalently bonded to the parent molecule through an —O— linkage. An example of an aryloxy is phenoxy.

The term "cycloalkoxy," as used alone or in combination herein, refers to a cycloalkyl group, as defined below, covalently bonded to the parent molecule through an —O— linkage.

The term "alkylthio," as used alone or in combination herein, refers to an alkyl group, as defined above, covalently bonded to the parent molecule through an —S— linkage.

The term "alkenyl," as used alone or in combination herein, refers to an alkyl group, as defined above, containing one or more carbon-carbon double bonds, preferably two or three double bonds. Examples of alkenyl include ethenyl, propenyl, 1,3-butadienyl, and 1,3,5-hexatrienyl.

The term "alkynyl," as used alone or in combination herein, refers to an alkyl group, as defined above, containing one or more carbon-carbon triple bonds, preferably one or two such triple bonds.

The term "cycloalkyl," as used alone or in combination herein, refers to an unsubstituted or optionally substituted, saturated cyclic hydrocarbon group containing three to eight carbon atoms. The cycloalkyl group may optionally be substituted by one or more substituents, and generally no more than three, and most often just one substituent. Preferred optional substituents include alkyl, halo, amino, mono- and di-substituted amino, aryl, hydroxy and the like.

The term "haloalkyl," as used alone or in combination herein, is a species of alkyl as defined herein, and particularly refers to an alkyl, preferably a lower alkyl, substituted with one or more halogen atoms, and preferably is a $C_1$ to $C_4$ alkyl substituted with one to three halogen atoms. One example of a haloalkyl is trifluoromethyl. Preferred examples of haloalkyl groups include trichloromethyl, triflouromethyl, and perflouroethyl.

The term "alkanoyl," as used alone or in combination herein, refers to an acyl radical derived from an alkanecarboxylic acid (alkyl-C(O)—), particularly a lower alkanecarboxylic acid, and includes such examples as acetyl, propionyl, butyryl, valeryl, and 4-methylvaleryl.

The term "aroyl," as used alone or in combination herein, means an acyl radical derived from an aromatic carboxylic acid, such as optionally substituted benzoic or naphthoic acids and specifically including benzoyl and 1-naphthoyl.

The term "aminocarbonyl," as used alone or in combination herein means an amino-substituted carbonyl (carbamoyl or carboxamide) wherein the amino group is a primary amino (—NH$_2$). Substituted aminocarbonyl refers to secondary (mono-substituted amino) or tertiary amino (disubstituted amino) group, as defined below, preferably having as a substituent(s) a lower alkyl group.

The term "aminoalkanoyl," as used alone or in combination herein, means an amino-substituted alkanoyl wherein the amino group is a primary amino group (-alkyl-C(O)—NH$_2$). The term "substituted aminoalkanoyl" refers to related secondary (mono-substituted amino) or tertiary amino (di-substituted amino) group, as defined below.

The term "carbocycloalkyl," as used alone or in combination herein, refers to an unsubstituted or optionally substituted, stable, saturated or partially unsaturated monocyclic, bridged monocyclic, bicyclic, or spiro ring carbocycle of 3 to 15 carbon atoms such as cyclopropyl, cyclobutyl, cyclopentyl, cyclohexyl, cycloheptyl, bicyclohexyl, bicyclooctyl, bicyclononyl, spirononyl and spirodecyl. Cycloalkyls are thus one specific subset of carbocycloalkyls. The term "optionally substituted" as it refers to "carbocycloalkyl" herein indicates that the carbocycloalkyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkylamido, (preferably a lower alkylamido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and/or lower alkoxy groups. Generally, there is no more than one optional substituent.

The term "heterocyclo," as used alone or in combination herein, refers to an unsubstituted or optionally substituted, stable, saturated, or partially unsaturated, monocyclic, bridged monocyclic, bicyclic, or spiro ring system containing carbon atoms and other atoms selected from nitrogen, sulfur and/or oxygen. Preferably, a heterocyclo group is a 5 or 6-membered monocyclic ring or an 8-11 membered bicyclic ring that consists of carbon atoms and contains one, two, or three heteroatoms selected from nitrogen, oxygen and/or sulfur. Heterocyclo includes bent-fused monocyclic cycloalkyl groups having at least one such heteroatom. The term "optionally substituted," as it refers to "heterocyclo" herein, indicates that the heterocyclo group may be substituted at one or more substitutable ring positions by one or more groups independently selected from alkyl (preferably lower alkyl and including haloalkyl (preferably trifluoromethyl)), alkoxy (preferably lower alkoxy), nitro, monoalkylamino (preferably a lower alkylamino), dialkylamino (preferably a di[lower]alkylamino), cyano, halo, alkanoyl, aminocarbonyl, monoalkylaminocarbonyl, dialkylaminocarbonyl, alkylamido (preferably lower alkylamido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Generally, there is no more than one optional substituent. The heterocyclo group may be, and generally is, attached to the parent structure through a carbon atom, or alternatively may be attached through any heteroatom of the heterocyclo group that results in a stable structure.

The term "heteroaryl," as used alone or in combination herein, refers to an unsubstituted or optionally substituted, stable, aromatic monocyclic or bicyclic ring system containing carbon atoms and other atoms selected from nitrogen, sulfur and/or oxygen. Preferably, a heteroaryl group is a 5- or 6-membered monocyclic ring (optionally benzofused) or an 8-11 membered bicyclic ring that consists of carbon atoms and contains one, two, or three heteroatoms selected from nitrogen, oxygen and/or sulfur. The term "optionally substituted" as it refers to "heteroaryl" herein indicates that the heteroaryl group may be substituted at one or more substitutable ring positions by one or more groups independently selected from alkyl (preferably lower alkyl and including haloalkyl (preferably trifluoromethyl)), alkoxy (preferably lower alkoxy), nitro, monoalkylamino (preferably a lower alkylamino), dialkylamino, (preferably a di[lower]alkylamino), cyano, halo, alkanoyl, aminocarbonyl, monoalkylaminocarbonyl, dialkylaminocarbonyl, alkylamido (preferably lower alkylamido), alkoxyalkyl (preferably a lower alkoxy[lower]alkyl), alkoxycarbonyl (preferably a lower alkoxycarbonyl), alkylcarbonyloxy (preferably a lower alkylcarbonyloxy), and aryl (preferably phenyl), said aryl being optionally substituted by halo, lower alkyl, and lower alkoxy groups. Generally, there is no more than one optional substituent. The heteroaryl group may be, and generally is attached to the parent structure through a carbon atom or alternatively may be attached through any heteroatom of the heteroaryl group that results in a stable structure. In the foregoing structures it is also contemplated that a nitrogen could be replaced with an N-oxide. Both heterocyclo and heteroaryl also are intended to embrace benzo fused structures such as 1,2-methylenedioxybenzene and 1,4-benzodioxan. Preferred examples of heteroaryl groups include pyridyl (e.g. 2-, 3-, or 4-pyridyl).

The terms "halo" and "halogen," as used alone or in combination herein, represent fluorine, chlorine, bromine or iodine, preferably fluorine or chlorine for enzyme affinity, and preferably chlorine, bromine, or iodine when a nucleofuge.

The term "aryl," as used alone or in combination herein, refers to an unsubstituted or optionally substituted monocyclic or bicyclic aromatic hydrocarbon ring system having 6 to 12 ring carbon atoms. Preferred are optionally substituted phenyl, 1-naphthyl, or 2-naphthyl groups. The aryl group may optionally be substituted at one or more substitutable ring positions (generally at no more than three positions and most often at one or two positions) by one or more groups independently selected from alkyl (including haloalkyl (preferably trifluoromethyl and difluoromethyl)), alkenyl, alkynyl, alkoxy, aryloxy, nitro, hydroxy, amino, mono- and di-substituted amino, cyano, halo, alkanoyl, aminocarbonyl, carboxylic acid, carboxylic acid esters, carboxylic acid amide, an optionally substituted phenyl (optionally substituted by halo, lower alkyl and lower alkoxy groups), heterocyclo, or heteroaryl. Preferably, the aryl group is phenyl optionally substituted with up to four and more usually with one or two groups, preferably selected from lower alkyl, lower alkoxy, as well as cyano, trifluoromethyl, and halo.

The terms "aralkyl" and "(aryl)alkyl," as used alone or in combination herein, are species of alkyl as defined herein, and particularly refer to an alkyl group as defined above in which one hydrogen atom is replaced by an aryl group as defined above, and include benzyl, and 2-phenylethyl.

The terms "(heterocyclo)alkyl" and "(heteroaryl)alkyl," as used alone or in combination can be considered a species of alkyl as defined herein, and particularly refer to an to an alkyl group as defined above in which one hydrogen atom is replaced by a heterocyclo group as defined above, or by a heteroaryl group as defined above.

The terms "alkoxycarbonyl," as used alone or in combination herein, mean a radical of the formula —C(O)-alkoxy, in which alkoxy is as defined above.

The term "alkylcarbonyloxy," as used alone or in combination herein, means a radical of the formula —O—C(O)-alkyl, in which alkyl is as defined above.

The term "alkoxyalkanoyl," as used alone or in combination herein, means a radical of the formula-alkyl-C(O)—O-alkyl.

The term "carboxyalkyl," as used alone or in combination herein, means a radical of the formula—alkyl-C(O)—OH.

The term "substituted amino," as used alone or in combination herein, embraces both mono and di-substituted amino. These terms, alone, or in combination, mean a radical of the formula —NR'R", where, in the case of mono-substitution, one of R' and R" is a hydrogen and the other is selected from alkyl, cycloalkyl, aryl, heterocyclo, (aryl)alkyl, (heterocyclo)alkyl, heteroaryl and hetero(aryl)alkyl; in the case of di-substitution, R' and R" are independently selected from alkyl, cycloalkyl, aryl, heterocyclo, and heteroaryl, or R' and R" together with the nitrogen atom to which they are both attached form a three to eight-membered heterocyclo or heteroaryl radical.

The term "amido," as used alone or in combination herein, refers to the group (—NH—) and the term "substituted amido" embraces a radical of the formula (—NR'—) where R' has the meaning above in connection with substituted amino.

The terms "alkanoylamido," "aroylamido," "heterocyclocarbonylamido" and "heteroaroylamido," as used alone or in combination herein, mean groups of the formula R—C(O)—NH— where R is an alkyl, aryl, heteroaryl or heterocyclo group. The terms "heteroaroyl" and "heterocyclocarbonyl," when used alone or in combination, mean groups of the formula R—C(O)— where R is a heteroaryl or heterocyclo group.

Unless otherwise defined, the term "optionally substituted" as used herein, refers to the substitution of a ring system at one or more positions with one or more groups selected from: $C_1$-$C_5$ alkyl, $C_1$-$C_5$ alkoxy, an optionally substituted phenyl, cyano, halo, trifluoromethyl, $C_1$-$C_5$ alkoxycarbonyl, $C_1$-$C_5$ alkyl carbonyloxy, mono- and bis-($C_1$-$C_5$alkyl)-carboxamide, $C_1$-$C_5$ alkylamido, nitro, and mono- and bis-($C_1$-$C_5$ alkyl) amino.

The terms "hydrophobic group" and "hydrophobic component" as used herein, refer to any of the groups hydrogen, alkyl, alkoxy, alkoxyalkyl, aryloxy, cycloalkoxy, alkylthio, alkenyl, alkynyl, cycloalkyl, haloalkyl, alkanoyl, aroyl, aminocarbonyl, aminoalkanoyl or optionally substituted aminoalkanoyl, carbocycloalkyl or optionally substituted carbocycloalkyl, heterocyclo or optionally substituted heterocyclo, heteroaryl or optionally substituted heteroaryl, halo, aryl, aralkyl, (heterocyclo)alkyl, (heteroaryl)alkyl, alkoxycarbonyl, alkylcarbonyloxy, alkoxyalkanoyl, carboxyalkyl, amino or substituted amino, amido or substituted amido, and alkanoylamido as defined above having at least some affinity for a hydrocarbon.

The terms "nucleofugal atom" and "nucleofugal group" as used herein refer to reactive leaving groups that, after reaction, can depart with a lone pair of electrons. Nucleofugal atoms or groups include halogen atoms (e.g. F, Cl, Br, and I) organosulfonyloxy groups (e.g. p-toluenesulfonyloxy, p-bromobenzenesulfonyloxy, methanesulfonyloxy, trifluoromethanesulfonyloxy, etc.), acyloxy groups (e.g. $CH_3CO_2$—, $CCl_3CO_2$—), aryloxy groups (e.g. phenyl-O—), imidazolyl groups, —O—N=O, —$NO_2$, —$OSO_3^-$, and —$OPO_2(OH)^-$.

It is recognized that there may be some overlap in some of the definitions of the various groups. Specific groups are mentioned, however, and may be particularly identified in the claims, in order to emphasize their positive inclusion in the described subject matter, as not only an optional substituent. As used herein, when a particular group, generally understood to have a single point of attachment to a core structure, such as an alkyl group, is identified in connection with a structure that must have two points of attachment in the structural core, it is understood that the named group (e.g., alkyl) refers to the parent group with a hydrogen or a site of unsaturation removed to create the second point of attachment so as to provide the required structure.

Compounds according to one embodiment of the present invention have the following generalized structural Formula I:

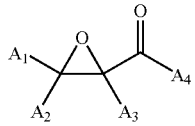

(Formula I)

or a pharmaceutically acceptable salt, prodrug, or ester thereof where $A_1$, $A_2$, and $A_3$, are independently selected from the group consisting of hydrogen, alkyl, alkoxy, alkoxyalkyl, aryloxy, cycloalkoxy, alkylthio, alkenyl, alkynyl, cycloalkyl, haloalkyl, alkanoyl, aroyl, aminocarbonyl, aminoalkanoyl or optionally substituted aminoalkanoyl, carbocycloalkyl or optionally substituted carbocycloalkyl, heterocyclo or optionally substituted heterocyclo, heteroaryl or optionally substituted heteroaryl, aryl, aralkyl, (heterocyclo)alkyl, (heteroaryl)alkyl, alkoxycarbonyl, alkylcarbonyloxy, alkoxyalkanoyl, and carboxyalkyl, and $A_4$ is selected from the group consisting of hydrogen, alkyl, alkoxy, alkoxyalkyl, aryloxy, cycloalkoxy, alkylthio, alkenyl, alkynyl, cycloalkyl, haloalkyl, alkanoyl, aroyl, aminocarbonyl, aminoalkanoyl or optionally substituted aminoalkanoyl, carbocycloalkyl or optionally substituted carbocycloalkyl, heterocyclo or optionally substituted heterocyclo, heteroaryl or optionally substituted heteroaryl, aryl, aralkyl, (heterocyclo)alkyl, (heteroaryl)alkyl, alkoxycarbonyl, alkoxyalkanoyl, carboxyalkyl, amino or substituted amino, amido or substituted amido, and $A_1$, $A_2$, $A_3$, and $A_4$ are not all hydrogen, since this would result in a compound lacking any specificity to the enzyme compared to the desired condition where at least one of these pendant groups has at least some specificity.

Preferably, at least one of $A_1$, $A_2$, $A_3$, and $A_4$ is a hydrophobic component designed to impart specificity of the substance for binding to and/or inactivation of FTase or GGTase. In this respect, in a preferred embodiment, $A_1$, $A_2$, $A_3$, and $A_4$ are independently selected from the group consisting of hydrogen, alkyl, alkenyl, alkynyl, aryl, aralkyl. For example, at least one of $A_1$, $A_2$, $A_3$, and $A_4$ is a branched alkenyl, which might be specifically a farnesyl or geranylgeranyl group. In this case, the prenylation enzyme inhibitor has a pendant group that matches that of the substrates for which FTase and GGTase, respectively, have affinity. In another preferred embodiment, the group $A_4$ is selected from the group consisting of hydrogen, alkyl (e.g. methyl), haloalkyl (e.g. trichloromethyl, triflouromethyl, perflouroethyl), aryl (e.g. phenyl), and heteroaryl (e.g. 4-pyridyl). These particular groups for $A_4$ result in an inhibitor having improved ability to react with the active site of a prenylation enzyme. More specifically, and without being bound to any particular theory, the presence of halogen atoms in the group $A_4$ enhances the reactivity of the inhibitor with epsilon amino groups found in the prenylation enzyme active sites, and particularly the lysine epsilon amino group found in the active site of FTase. Additionally, the presence of phenyl and pyridyl groups enhance the stability of a Schiff base or imine that is believed to result from reaction of the inhibitor with the enzyme. From the above explanation, a particularly preferred variant of the prenylation enzyme inhibitor of the present invention according to Formula I is one in which at least one of $A_1$, $A_2$, and $A_3$ is a hydrophobic group (e.g. a farnesyl or a geranylgeranyl group) and $A_4$ is selected from the group consisting of alkyl, haloalkyl, aryl, and heteroaryl.

Possible methods of synthesizing prenylation inhibitor compounds of the present invention are provided below for compounds according to Formula I and Formula II as described above. In the case of alpha-oxo epoxides within the scope of Formula I, the treatment of the alpha,beta-unsaturated carbonyl compound with alkaline hydrogen peroxide, is depicted below:

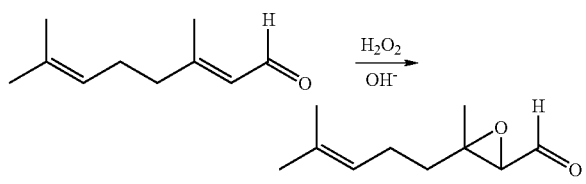

Another synthesis possibility for compounds of Formula I is the Sharpless epoxidation of the allylic alcohol, followed by oxidation of the alcohol. This method results in the stereospecific formation of chiral alpha-oxo epoxides, and is depicted below:

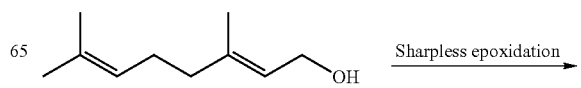

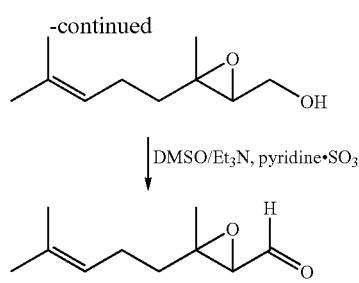

Another class of compounds contemplated within the scope of the invention has the following generalized structural Formula II:

A-Y—(C=Z)—CX$_1$X$_2$X$_3$   (Formula II)

or a pharmaceutically acceptable salt, prodrug, or ester thereof where Y is a heteroatom or heteroatomic group selected from the group consisting of O, NH, NA', and S; where, when Y is O, A and A' are independently selected from the group consisting of hydrogen, alkyl, alkoxyalkyl, alkylthio, alkenyl, alkynyl, cycloalkyl, haloalkyl, carbocycloalkyl or optionally substituted carbocycloalkyl, heterocyclo or optionally substituted heterocyclo, heteroaryl or optionally substituted heteroaryl, aryl, aralkyl, (heterocyclo)alkyl, (heteroaryl)alkyl, carboxyalkyl, amino or substituted amino, amido or substituted amido, and alkanoylamido;

when Y is S, A and A' are independently selected from the group consisting of hydrogen, alkyl, alkoxy, alkoxyalkyl, aryloxy, cycloalkoxy, alkylthio, alkenyl, alkynyl, cycloalkyl, haloalkyl, carbocycloalkyl or optionally substituted carbocycloalkyl, heterocyclo or optionally substituted heterocyclo, heteroaryl or optionally substituted heteroaryl, aryl, aralkyl, (heterocyclo)alkyl, (heteroaryl)alkyl, carboxyalkyl, amino or substituted amino, amido or substituted amido, and alkanoylamido; and, when Y is NH or NA', A and A' are independently selected from the group consisting of hydrogen, alkyl, alkoxy, alkoxyalkyl, aryloxy, cycloalkoxy, alkylthio, alkenyl, alkynyl, cycloalkyl, haloalkyl, alkanoyl, aroyl, aminocarbonyl, aminoalkanoyl or optionally substituted aminoalkanoyl, carbocycloalkyl or optionally substituted carbocycloalkyl, heterocyclo or optionally substituted heterocyclo, heteroaryl or optionally substituted heteroaryl, halo, aryl, aralkyl, (heterocyclo)alkyl, (heteroaryl)alkyl, alkoxycarbonyl, alkylcarbonyloxy, alkoxyalkanoyl, carboxyalkyl, amino or substituted amino, amido or substituted amido, and alkanoylamido;

Z is O or S, resulting in a carbonyl or thiocarbonyl group; and,

X$_1$, X$_2$, and X$_3$ are independently selected from the group consisting of hydrogen, halogen, organosulfonyloxy, bromobenzenesulfonyloxy, methanesulfonyloxy, trifluoromethanesulfonyloxy, acyloxy, aryloxy, imidazolyl, —O—N=O, —NO$_2$, —OSO$_3^-$, and —OPO$_2$(OH)$^-$. The groups X$_1$, X$_2$, and X$_3$ are not all hydrogen, as this particular case would result in the compound having an attached methyl group which is relatively unreactive compared to the desired condition where at least one of these pendant groups is a nucleofugal group. In a preferred embodiment, A, and optionally A', are independently selected from the group consisting of hydrogen, alkyl, alkenyl, alkynyl, aryl, aralkyl. In another preferred embodiment, at least one of A, and optionally A' is a branched alkenyl, which may be specifically a farnesyl or geranylgeranyl group.

According to the possibilities for Formula II, there exists a carbonyl variation, where Z is oxygen, and also a thiocarbonyl variation, where Z is sulfur. Preferred enzyme inhibitor compounds within the generalized structural Formula II can be characterized as alpha-haloesters or alpha-halothioesters where Y is an oxygen atom, X$_1$ and X$_2$ are hydrogen, and X$_3$ is a halogen. In the case of the carbonyl variation of Formula II, a preferred class of prenylation inhibitors is obtained when X$_1$ is oxygen, such that the inhibitor will now have two carbonyl functions, and X$_2$ is methyl. These preferred compounds may also be categorized as pyruvic acid derivatives.

As mentioned, the portion of the compound represented by any of A aids in the selective, noncovalent binding or affinity of the inventive compounds for prenyltransferases. Also, the carbonyl or thiocarbonyl group of compounds represented by Formula II, combined with an adjacent nucleofuge-bearing carbon atom, can subsequently bond to the prenyltransferase active site, thereby regulating the level of activity of the prenyltransferase by hampering access of substrates to the active site residues and/or other mechanisms such as by inducing conformational changes in the prenyltransferase that affect its catalytic ability. The regulation of catalytic activity of the prenyltransferase can also be achieved by total inactivation of a portion of the prenyltransferase molecules while leaving some molecules completely unmodified.

It is possible to prepare compounds within the scope of Formula II according to the pathway provided below, where, for example, A is a farnesyl subsitutent, Y and Z are oxygen, X$_1$ and X$_2$ are hydrogen, and X$_3$ is bromine:

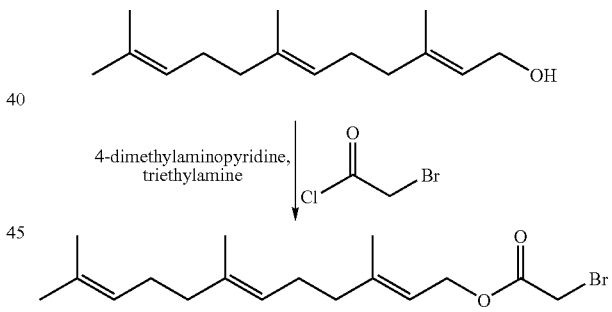

The pathway outlined below depicts the synthesis of another compound of Formula II, having a hydrophobic substituent comprising a phenyl group and a polyether functionality:

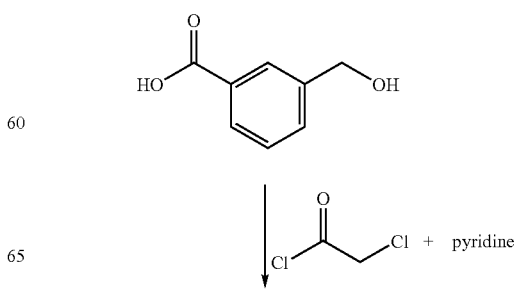

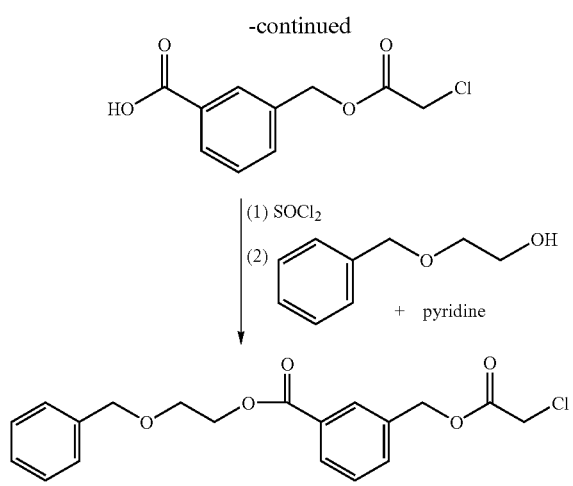

Other embodiments of the invention include a pharmaceutically acceptable salt, prodrug, or ester of the compounds of Formula I or Formula II. By way of example, for compounds having structural Formula II, the carbonyl groups can be masked in various forms including a hydrate [C(OH)$_2$], a hemiacetal or hemiketal [C(OH)(OR')], an acetal or a ketal [C(OR')(OR")], an acylal or related compound [C(OC(=O)R')OC(=O)R")], a bisulfite addition compound [C(OH)(SO$_3^-$)], an enol (C=COH), an enol ether (C=COR'), an enol ester [C=COC=(=O)R'], and so forth, wherein R' and R" are independently selected from the group consisting of hydrogen, alkyl, alkoxy, alkoxyalkyl, aryloxy, cycloalkoxy, alkylthio, alkenyl, alkynyl, cycloalkyl, haloalkyl, alkanoyl, aroyl, aminocarbonyl, aminoalkanoyl or optionally substituted aminoalkanoyl, carbocycloalkyl or optionally substituted carbocycloalkyl, heterocyclo or optionally substituted heterocyclo, heteroaryl or optionally substituted heteroaryl, halo, aryl, aralkyl, (heterocyclo)alkyl, (heteroaryl)alkyl, alkoxycarbonyl, alkylcarbonyloxy, alkoxyalkanoyl, carboxyalkyl, amino or substituted amino, amido or substituted amido, and alkanoylamido. Likewise, prenylation enzyme inhibitors according to the thiocarbonyl variation of Formula II may also include masked thiocarbonyl groups, in which the oxygen atoms in the masked groups according to the above description are replaced by sulfur atoms. Of course, it is possible that, where the masked groups according to the above description contain more than one oxygen atom, a combination of oxygen and sulfur atoms may actually be included in the masked group. Such masked carbonyl or thiocarbonyl groups may produce the carbonyl or thiocarbonyl groups of the prenylation enzyme inhibitors of the present invention under physiological conditions.

Some cancer cells in which farnesylation of Ras is blocked alternatively employ the related prenylation reaction geranylgeranylation to attach a hydrophobic group to Ras, accomplishing membrane localization and continued cancerous behavior of the cell. The enzyme that attaches the geranylgeranyl group to Ras protein to facilitate localization at the inner surface of the cancer cell membrane is geranylgeranyl protein transferase, also known as protein geranylgeranyltransferase (referred to here as GGTase). The geranylgeranyl group becomes attached to Ras by reaction with geranylgeranyl diphosphate, also known as geranylgeranyl pyrophosphate (referred to here as GGPP). Stated otherwise, GGTase catalyzes the following reaction, in which Ras becomes attached to geranylgeranyl group by displacement of pyrophosphate ($P_2O_7^{4-}$, referred to here as PP$_i$):

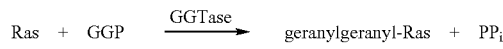

The newly formed geranylgeranyl-Ras localizes at the inner surface of the cancer cell membrane and causes the cancer cell to divide without restraint. Thus, a key target in a strategy to retard cancer cell proliferation is the enzyme GGTase. By reducing or destroying GGTase activity, either in combination with regulation of Ras farnesylation or independently, Ras geranylgeranylation may be also regulated, which in turn should further hinder the ability of the cancer cell to divide and proliferate through localization of Ras at its inner membrane surface. As noted previously, regulation of RhoB geranlygeranylation by use of inhibitors of the present invention is also contemplated as a means for retarding and/or terminating cancer cell growth.

To more precisely align the structure of the inhibitors of the present invention with the active sites of FTase, GGTase, or other enzymes, variation of the distance between the covalent-bonding group and the farnesyl-mimicking or geranylgeranyl-mimicking group is achieved through altering the length of a "spacer" between such groups. For example, inhibitors representative of the carbonyl variation of structural Formula II may be more precisely tailored to inhibit either FTase or GGTase activity by altering the spacer length as represented below:

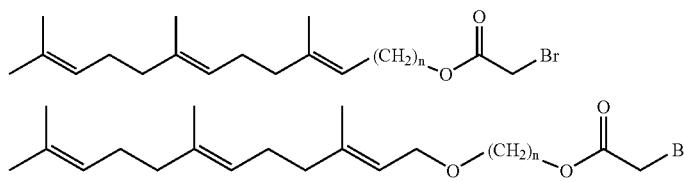

Targeted for FTase

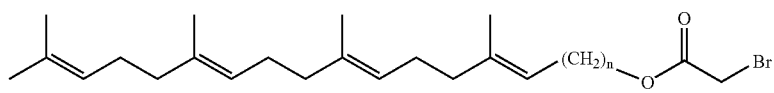

-continued

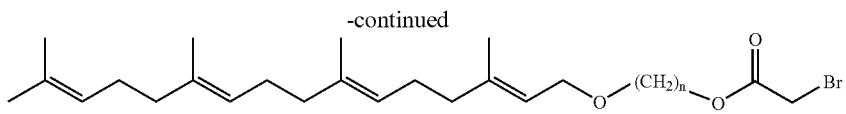

Targeted for GGTase where the value of n, representing the number of carbon atoms between the respective farnesyl and geranylgeranyl groups, will generally range from 0 to about 10, although instances where longer chains are required for alignment with other types of enzymes are readily recognizable to the ordinary skilled artisan having regard for this disclosure.

Inhibitors of the present invention may also incorporate an aromatic group for enhanced binding to the hydrophobic binding site of FTase or GGTase. Such compounds are exemplified by the following specific enzyme inhibitors according to the carbonyl variation of structural Formula II, although numerous other possible embodiments of this type of compound are of course possible and readily apparent to one of ordinary skill in the art, having regard for this disclosure:

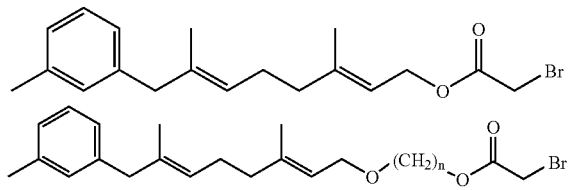

Three additional possibilities are represented below, where the last two have an A group that is selective for the FTase active site over the GGTase and squalene synthase active sites, thus conferring added specificity for the desired target enzyme.

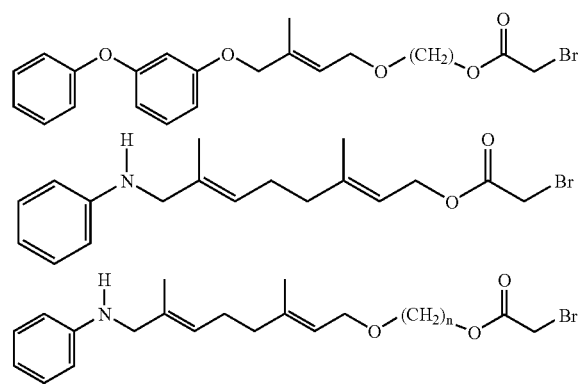

The inhibitors of the present invention are applicable in particular to the reduction in prenylation activity of the enzymes farnesyl protein transferase and geranylgeranyl protein transferase. Without wishing to be bound by any particular theory or reaction mechanism, a hypothetical pathway illustrating FTase inhibition using the alpha-oxo epoxide prenylation enzyme inhibitors, according to Formula I of the present invention, is shown below:

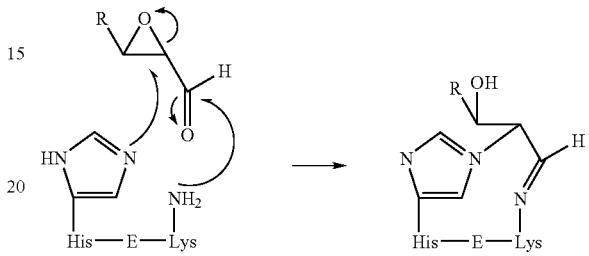

As shown, the FTase active site contains two amino acid residues that are involved in the reaction with the inhibitor, namely His-248 and Lys-294. The rest of the enzyme is conveniently represented as E. These two residues are in close proximity as a consequence of their normal role in binding the natural substrate FPP at its terminal phosphate. As shown above, nucleophilic attack by the His imidazole group results in epoxide ring opening, thus making the epoxide oxygen formally a nucleofuge. In addition to alkylation of the imidazole ring, the nearby epsilon-amino group of the Lys forms a Schiff base or imine with the aldehyde group of the alpha-oxo epoxide. The result of the above reactions is the crosslinking of two active site residues. The resulting crosslinked structure irreversibly precludes the FTase active site residues from catalyzing prenylation reactions, thus impairing the enzyme's overall functioning.

Analogous reaction mechanisms can be postulated for inhibitor compounds of the present invention according to both the carbonyl and thiocarbonyl variations of Formula II. In these cases, the nucleofugal atom or group adjacent to a carbonyl group can react with the aforementioned active site residues to crosslink them in an analogous manner to the mechanism shown above, with an accompanying release of the nucleofugal group.

Preferably, the inhibitor is administered under proper conditions and in a concentration such that its presence in the prenylation system reduces prenylation activity by at least about 50%, more preferably at least about 75%, and even more preferably by at least about 90%. Pharmaceutical formulations can be prepared by combining appropriate amounts of the inhibitor in a pharmaceutically acceptable carrier, diluent, or excipient. In such formulations, the inhibitor is typically present in an amount from about 0.1-20% by weight, and more commonly from about 1-10%.

Combinations of this invention with other anticancer agents to produce synergistic effects of benefit to the patient are also possible. This might be based on two strategies. One is to interfere with different biochemical processes to increase tumor cell killing. Another is to hamper development of drug resistance, which is less likely to occur simultaneously in tumor cells exposed to anticancer agents based on interference with different biochemical pathways in the tumor cells.

In summary an improved method of interference with protein prenylation in tumor cells has been described that may prevent or hamper the proliferation of tumor cells, possibly resulting in a decrease in tumor size and/or disappearance of the cancer, to the benefit of cancer patients.

EXAMPLES 1-2

Two alpho-oxo epoxides according to Formula I of the present invention were synthesized according to procedures set forth in H. Yao and D. E. Richardson, J. Am. Chem. Soc. 2000, 122, 3220-3221 and also in C. A. Bunton and G. J. Minkoff, J. Chem. Soc. 1949, 665-670. The compounds were then tested for their inhibition of the growth of various cancer cells. These compounds had, as their $A_2$ substituent, farnesyl and geranylgeranyl groups, respectively. These inhibitors had structural formulas as shown below.

EXAMPLE 1

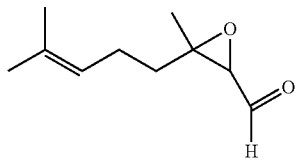

EXAMPLE 2

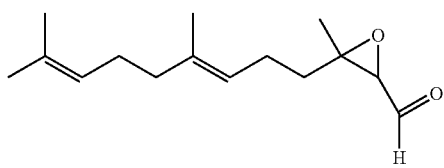

The compounds were tested for growth inhibition in a variety of human cancer cell lines, according to procedures described by K. J. Okolotowicz, W. L. Lee, R. F. Hartman, S. R. Lefler, and S. D. Rose, *Inactivation of Protein Farnesyltransferase by Active-Site-Targeted Dicarbonyl Compounds*, Arch. Pharm. Pharm. Med. Chem. 2001, 334, 194-202. Results of biological testing of these compounds are summarized in Table 1, where the $GI_{50}$ value represents the concentration of inhibitor compound required to effect a 50% reduction in cell growth (i.e. 50% inhibition).

TABLE 1

Inhibition of Cancer Cell Growth by Alpha-oxo Epoxides

| Human cancer cell line | $GI_{50}$/molar Compound RG-22 | $GI_{50}$/molar Compound RG-23 |
|---|---|---|
| Breast (MCF-7) | $14 \times 10^{-6}$ | $8.9 \times 10^{-6}$ |
| Prostate (DU-145) | $27 \times 10^{-6}$ | $28 \times 10^{-6}$ |
| Central nervous syst. (SF268) | $30 \times 10^{-6}$ | $42 \times 10^{-6}$ |
| Pancreatic (BXPC-3) | $67 \times 10^{-6}$ | $51 \times 10^{-6}$ |
| Colon (KM20L2) | $95 \times 10^{-6}$ | $61 \times 10^{-6}$ |
| Lung (NCI-H460) | $117 \times 10^{-6}$ | $63 \times 10^{-6}$ |

Results show that both compounds are extremely active for inhibiting cell growth in various human cancer cell lines in culture. In fact, one of the $GI_{50}$ values was below 10 micromoles/liter. Additionally, the compounds were active against mouse P388 leukemia cells in culture. In these cases, compound RG-22 exhibited an $ED_{50}$ of $26 \times 10^{-6}$ M, and RG-23 exhibited an $ED_{50}$ of only $11 \times 10^{-6}$ M. Based on these results, the anticancer activity of these compounds is confirmed.

EXAMPLES 3-4

Two alpha-halo carbonyl compounds were also synthesized as decribed previously herein and tested for their inhibition of the growth of various cancer cells. These compounds had substituent farnesyl groups as well as substituent nucleofugal halogen atoms. The inhibitors had structural formulas as shown below:

EXAMPLE 3

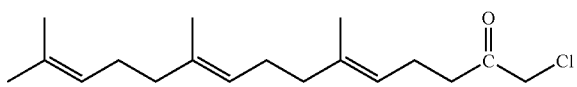

EXAMPLE 4

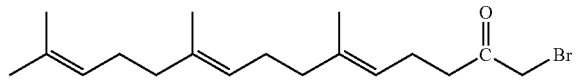

The compounds were tested for growth inhibition in a variety of human cancer cell lines, as described in Examples 1-2. Results of the in vitro cell culture testing of these compounds are summarized in Table 2, which provides the associated $GI_{50}$ values.

TABLE 2

Cell Culture Results with Alpha-halo Carbonyl Compounds

| Human cancer cell line | Example 3 $GI_{50}$/molar | Example 4 $GI_{50}$/molar |
|---|---|---|
| Colon (HT-29) | $10^{-4}$ to $10^{-5}$ | $10^{-4}$ to $10^{-5}$ |
| Colorectal (Colo-205) | $10^{-4}$ to $10^{-5}$ | $10^{-4}$ to $10^{-5}$ |
| NSC Lung (H-460) | $1.1 \times 10^{-5}$ | $1.4 \times 10^{-5}$ |
| Prostate (PC-3) | $7.9 \times 10^{-6}$ | $1.6 \times 10^{-5}$ |
| Acute myeloid leukemia (HL-60) | Above $10^{-4}$ | $10^{-9}$ to $10^{-10}$ |
| Fibrosarcoma (HT-1080) | $10^{-5}$ to $10^{-6}$ | $10^{-4}$ to $10^{-5}$ |
| Urinary bladder (T-24) | $10^{-4}$ to $10^{-5}$ | $10^{-4}$ to $10^{-5}$ |
| Colon (Caco-2) | Above $10^{-4}$ | $10^{-4}$ to $10^{-5}$ |

Again, results show that the compounds provide effective inhibition of cancer cell growth, even at low concentrations.

What is claimed is:

1. A compound of Formula IIA':

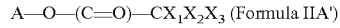

A—O—(C=O)—CX$_1$X$_2$X$_3$ (Formula IIA')

wherein A is selected from the group consisting of

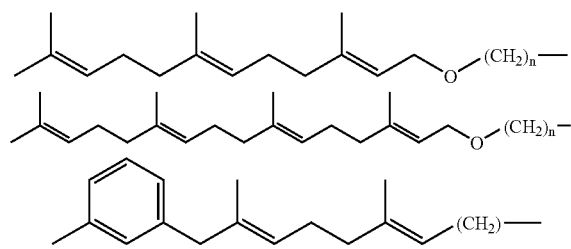

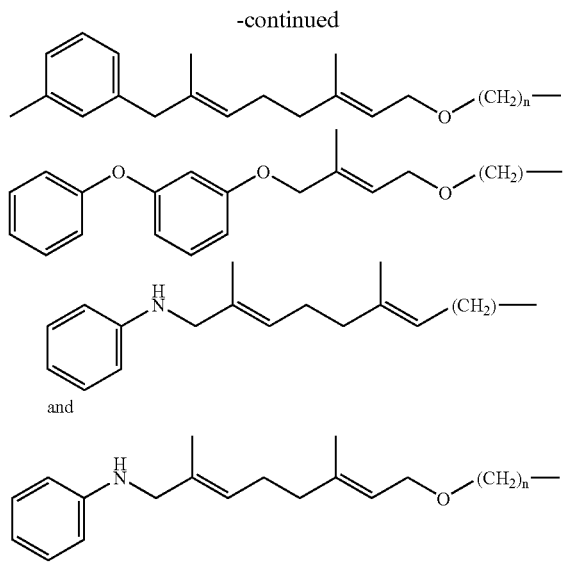

wherein n is an integer from 0 to about 10; and $X_1$, $X_2$, and $X_3$ are independently selected from the group consisting of hydrogen, halogen, organosulfonyloxy, bromobenzenesulfonyloxy, methanesulfonyloxy, trifluoromethanesulfonyloxy, acyloxy, aryloxy, imidazolyl, —O—N=O, —NO$_2$, —OSO$_3^-$, and —OPO$_2$(OH)$^-$, with the proviso that $X_1$, $X_2$, and $X_3$ are not all hydrogen, or a pharmaceutically acceptable salt, prodrug, or ester thereof.

2. A pharmaceutical composition comprising a compound of claim 1 and a pharmaceutically acceptable carrier; diluent, or excipient.

3. A method of inhibiting a prenylation enzyme comprising contacting the enzyme with a compound of claim 1.

4. A method of treating cancer comprising administering an effective amount of a pharmaceutical composition of claim 2.

* * * * *